US012564714B2

(12) United States Patent
Chung et al.

(10) Patent No.: US 12,564,714 B2
(45) Date of Patent: Mar. 3, 2026

(54) REVERSE ELECTRODIALYSIS DEVICE USING PRECIPITATION REACTION, AND DRUG INJECTION DEVICE USING SAME

(71) Applicant: Seoul National University R&DB Foundation, Seoul (KR)

(72) Inventors: Taek-Dong Chung, Gwacheon-si (KR); Jeong-Se Yun, Seoul (KR); Song-Yi Yeon, Geoje-si (KR)

(73) Assignee: Seoul National University R&DB Foundation, Seoul (KR)

( * ) Notice: Subject to any disclaimer, the term of this patent is extended or adjusted under 35 U.S.C. 154(b) by 538 days.

(21) Appl. No.: 18/062,191

(22) Filed: Dec. 6, 2022

(65) Prior Publication Data

US 2023/0098453 A1 Mar. 30, 2023

Related U.S. Application Data

(62) Division of application No. 16/625,406, filed as application No. PCT/KR2018/007185 on Jun. 25, 2018, now Pat. No. 11,565,106.

(30) Foreign Application Priority Data

Jun. 28, 2017 (KR) ........................ 10-2017-0082019

(51) Int. Cl.
| | |
|---|---|
| *A61N 1/30* | (2006.01) |
| *A61M 37/00* | (2006.01) |
| *A61N 1/04* | (2006.01) |
| *A61N 1/24* | (2006.01) |
| *H01M 8/22* | (2006.01) |
| *H01M 8/2455* | (2016.01) |

(52) U.S. Cl.
CPC .............. *A61N 1/30* (2013.01); *A61M 37/00* (2013.01); *A61N 1/24* (2013.01); *H01M 8/227* (2013.01); *H01M 8/2455* (2013.01); *A61N 1/0444* (2013.01)

(58) Field of Classification Search
CPC .......... A61N 1/30; A61N 1/0444; A61N 1/24; A61M 37/00; H01M 8/227; H01M 8/2455
See application file for complete search history.

(56) References Cited

U.S. PATENT DOCUMENTS

| | | | |
|---|---|---|---|
| 5,637,084 | A | 6/1997 | Kontturi et al. |
| 2006/0060532 | A1 | 3/2006 | Davis |
| 2007/0295604 | A1 | 12/2007 | Freydina |
| 2009/0314718 | A1 | 12/2009 | Sparrow et al. |
| 2011/0117395 | A1 | 5/2011 | Roodenburg |
| 2013/0288142 | A1 | 10/2013 | Fu et al. |
| 2016/0002082 | A1 | 1/2016 | Yin et al. |

FOREIGN PATENT DOCUMENTS

| | | | | |
|---|---|---|---|---|
| JP | 2011-517012 | A | 5/2011 | |
| KR | 10-2011-0034006 | A | 4/2011 | |
| KR | 10-2016-0139760 | A | 12/2016 | |
| KR | 10-2017-0002362 | A | 1/2017 | |
| KR | 10-2017-0036832 | A | 4/2017 | |
| WO | WO-2016056778 | A1 * | 4/2016 | ............ A61M 37/00 |

OTHER PUBLICATIONS

Gherasim, C.-V. et al, "Investigation of batch electrodialysis process for removal of lead ions from aqueous solutions", Chemical Engineering Journal 256 (2014) 324-334.
Marder, L. et al. "Removal of Cadmium and Cyanide from Aqueous Solutions through Electrodialysis", J. Braz. Chem. Soc., vol. 14, No. 4, 610-615, 2003.
Choi, et al. "Tunable reverse electrodialysis microplatform with geometrically controlled self-assembled nanoparticle network", Lab Chip (2015) 15, 168-178.
International Search Report and Written Opinion for corresponding Patent Application No. PCT/KR2018/007185 dated Oct. 2, 2018.

* cited by examiner

*Primary Examiner* — Robert A Wax
*Assistant Examiner* — William Craigo
(74) *Attorney, Agent, or Firm* — Renner, Otto, Boisselle & Sklar, LLP

(57) ABSTRACT

A reverse electrodialysis device using a precipitation reaction, according to one embodiment of the present invention, comprises a first cell stack alternately forming solid salt chambers and precipitation chambers through cation-exchange membranes and anion-exchange membranes which are alternately provided, and a first water-soluble solid salt and a second water-soluble solid salt which are filled in the solid salt chambers, wherein the first water-soluble solid salt and the second water-soluble solid salt are alternately filled in the solid salt chambers, and can react with each other so as to generate a precipitate in neighboring precipitation chambers when water is supplied.

6 Claims, 4 Drawing Sheets

REVERSE ELECTRODIALYSIS DEVICE USING PRECIPITATION REACTION, AND DRUG INJECTION DEVICE USING SAME

RELATED APPLICATION DATA

This application is a division of U.S. patent application Ser. No. 16/625,406 filed Dec. 20, 2019, which is a national phase of International Application No. PCT/KR2018/007185, filed Jun. 25, 2018, and published in Korean under International Publication No. 2019/004683 A1 on Mar. 1, 2019, which claims the benefit of Korean Patent Application No. 10-2017-0082019, filed Jun. 28, 2017, all of which are incorporated herein by reference.

TECHNICAL FIELD

The present disclosure relates to a reverse electrodialysis device using a precipitation reaction and a drug injection device using the same.

BACKGROUND ART

A reverse electrodialysis device (RED) is a device to produce electrical energy, which uses the principle of electrodialysis reversed, including the removal of ions in a solution by electricity. Specifically, such a reverse electrodialysis device includes a cell stack in which cation-exchange membranes and anion-exchange membranes are alternately disposed. As low-salinity water and high-salinity water alternately enter the cell stack, a flow of ions is created to produce electrical energy.

A difference between concentrations of the high-salinity water and the low-salinity water should be maintained to continuously obtain electrical energy from such a reverse electrodialysis device. Accordingly, a pump is required to continuously supply the high-salinity water and the low-salinity water, which causes difficulties in miniaturizing such a device.

In addition, a conventional drug injection device using a reverse electrodialysis device cannot deliver a drug for a long period of time because a voltage decreases rapidly, depending on time.

As a technology related to a reverse electrodialysis device, for example, a solid salt reverse electrodialysis device is disclosed in Korean Patent Publication No. 10-2017-0036832 published on Apr. 3, 2017.

DISCLOSURE

Technical Problem

An aspect of the present disclosure is to provide a reverse electrodialysis device which may maintain a concentration of low-salinity water at a low concentration to maintain a maximum open-circuit voltage at a constant level and may be miniaturized without a requirement for an additional pump.

Another aspect of the present disclosure is to provide a drug injection device, having improved performance, which may deliver a drug to skin for a long period of time using the principle of the above-mentioned reverse electrodialysis device.

Technical Solution

According to an aspect of the present disclosure, a reverse electrodialysis device includes a first cell stack in which a solid salt chamber and a precipitation chamber are alternately formed through a cation-exchange membrane and an anion-exchange membrane mounted alternately and first water-soluble solid salt and second water-soluble salt filling the solid salt chamber. The first water-soluble solid salt and the second water-soluble salt alternately fill the solid salt chamber and react with each other to generate a precipitate in the precipitation chamber when water is supplied.

According to another aspect of the present disclosure, a drug injection device includes a reverse electrodialysis device generating current through a precipitation reaction between first water-soluble solid salt and second water-soluble solid salt and a material injection unit including a material having a charge or polarity and configured to inject the material having a charge or polarity into the skin by current generated by the reverse electrodialysis device. The reverse electrodialysis device includes a first cell stack in which a solid salt chamber and a precipitation chamber are alternately formed through a cation-exchange membrane and an anion-exchange membrane mounted alternately and first water-soluble solid salt and second water-soluble solid salt filling the solid salt chamber. The water-soluble solid salt and the second water-soluble solid salt alternately fill the solid salt chamber and react with each other to generate a precipitate in the precipitation chamber when water is supplied.

ADVANTAGEOUS EFFECTS

As set forth above, according to an embodiment, a solid salt chamber of a cell stack is alternately filled with first water-soluble solid salt and second water-soluble solid salt. When water is supplied, the first water-soluble solid salt and the second water-soluble solid salt react with each other in a precipitation chamber to produce a precipitation.

Thus, a concentration of low-salinity water may be maintained at a low concentration to maintain a maximum open-circuit voltage at a constant level. In addition, since an additional pump is not required, miniaturization of a device may be achieved.

Moreover, according to an embodiment, by applying the principle of a reverse electrodialysis device using a precipitation production reaction to a drug injection device, a drug may be delivered to skin for a long period of time to improve performance of a device.

BEST MODE FOR INVENTION

Figure 1:
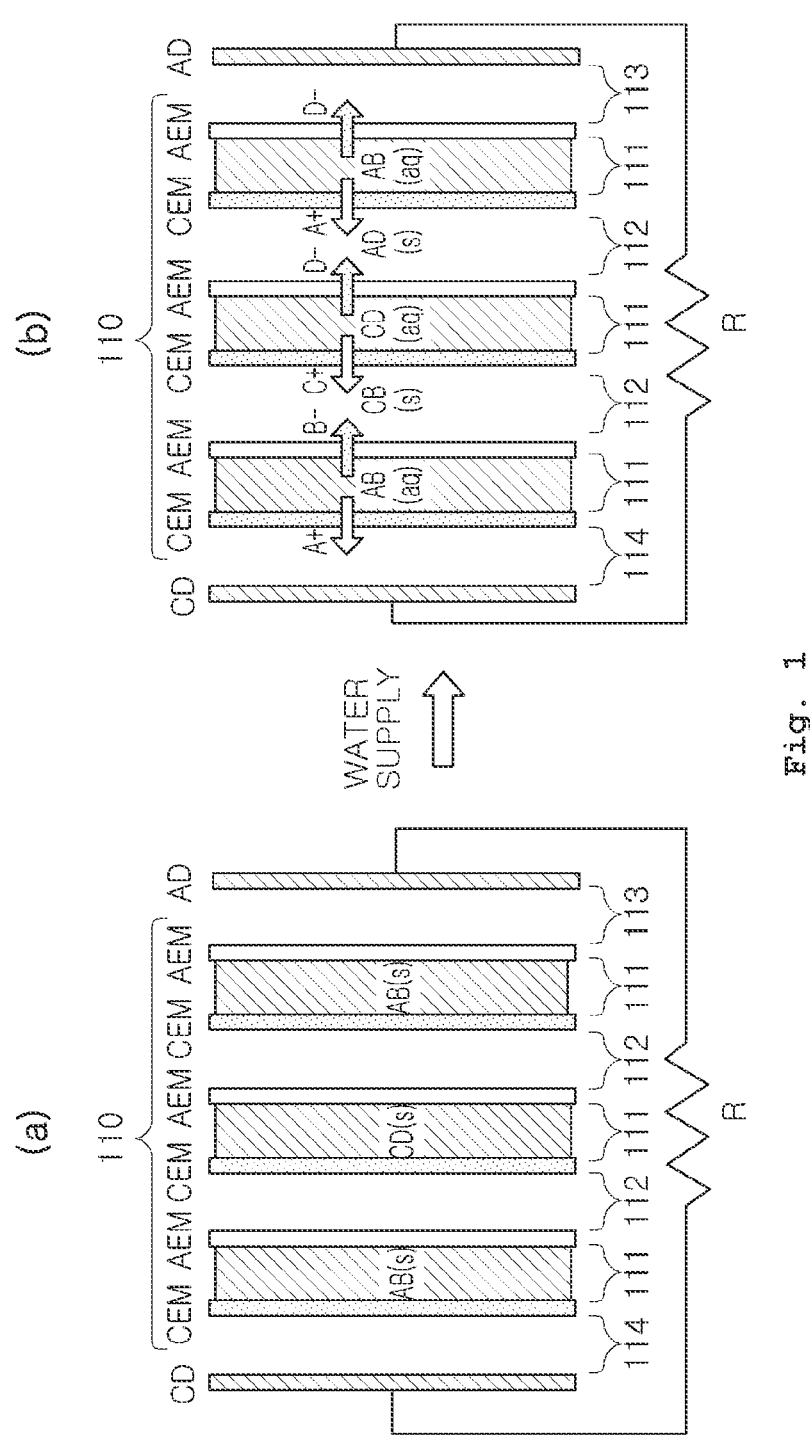
FIG. 1 illustrates a reverse electrodialysis device using a precipitation reaction according to an embodiment of the present disclosure.

Hereinafter, embodiments of the present disclosure will be described with reference to the accompanying drawings. However, the embodiments of the present disclosure may be modified in various forms, and the scope of the present disclosure is not limited to the embodiments. In the drawings, the shapes and dimensions of elements may be exaggerated for clarity, and the same reference numerals will be used throughout to designate the same or like elements.

FIG. 1 illustrates a reverse electrodialysis device using a precipitation reaction according to an embodiment of the present disclosure. FIG. 1($a$) illustrates a reverse electrodialysis device before water is supplied, and FIG. 1($b$) illustrates a process of generating a precipitate in a reverse electrodialysis device after the water is supplied.

As illustrated in FIG. 1($a$), the reverse electrodialysis device using a precipitation reaction according to an embodiment may include a first cell stack 110, in which a solid salt chamber 111 and a precipitation chamber 112 are alternately formed, and two types kinds of water-soluble solid salts, for example, AB(s) and CD(s), filling the first cell stack 110, and may include anodes AD, cathodes CD, an oxidation chamber 113, and a reduction chamber 114.

Specifically, in the first cell stack 110, a solid salt chamber 111 and a precipitation chamber 112 may be alternately formed through a cation-exchange membrane CEM and an anion-exchange membrane AEM mounted alternately to be spaced apart from each other at regular intervals. In FIG. 1, only three solid salt chambers 111 and two precipitation chambers 112 are illustrated as an example for better understanding of the present disclosure, and it will be apparent to those skilled in the art that the number of the solid salt chambers 111 may be modified as necessary.

Since the cation-exchange membrane CEM is negatively charged, ions possessing negative charges do not permeate therethrough as they are repelled by the cation-exchange membrane CEM, and only ions posses sing positive charges may pass therethrough. Meanwhile, since the anion-exchange membrane AEM is positively charged, ions possessing positive charges do not pass therethrough as they are repelled by the anion-exchange membrane AEM, and only ions possessing negative charges may pass therethrough.

In the present disclosure, a space between the cation-exchange membrane CEM and the anion-exchange membrane AEM will be referred to as a "chamber."

As illustrated in FIG. 1, the solid salt chamber 111 and the precipitation chamber 112 may be alternately formed in the order of a solid salt chamber-a precipitation chamber-a solid salt chamber-a precipitation chamber-a solid salt chamber. In addition, two types of water-soluble solid salt, for example, first water-soluble solid salt AB(s) and second water-soluble solid salt CD(s) may alternately fill the solid salt chamber 111. These chambers may be configured to prevent solid salts therein from escaping therefrom.

In addition, when water is supplied, the first water-soluble solid salt AB(s) and the second water-soluble solid salt CD(s) may react with each other to generate a precipitate in a neighboring precipitation chamber 112.

Specifically, when water is supplied, cations A+ of the first water-soluble solid salt AB(s) may pass through the cation-exchange membrane CEM and anions D⁻ of the second water-soluble solid salt CD(s) may pass through the anion-exchange membrane AEM. The cations A+ and the anions D⁻ may be precipitated in a neighboring precipitation chamber 112 while generating a precipitate AD(s) therein. Similarly, anions B⁻ of the first water-soluble solid salt AB (s) and cations C+ of the second water-soluble solid salt CD(s) may be precipitated in the neighboring precipitation chamber 112 while generating a precipitate CB(s) therein.

The precipitate, generated by the first water-soluble solid salt AB (s) and the second water-soluble solid salt CD (s), may include at least two of Ac $(OH)_2$, $Al(OH)_3$, $As_2S_3$, $AgN_3$, AgBr, AgCl, AgCN, $Ag_2C_2O_4$, $Ba_3(AsO_4)_2$, $BaCO_3$, $BaCrO_4$, $Ba_2Fe(CN)_6$, $BaSO_4$, $BiASO_4$, $Bi(OH)_3BiI_3$, $BiPO_4Bi_2S_3$, $Cd_3(ASO_4)_2$, $CdCO_3$, $Cd_2Fe(CN)_6$, $Cd(OH)_2$, $Cd_3(PO_4)_2$, CdS, $Ca_3(ASO_4)_2$, $CaCO_3$, $CaC_2O_4$, $Ce(OH)_3$, $CePO_4$, $Ce(OH)_4$, $CoC_2O_4$, CuCN, CuOH, CuI, $Cu_2S$, CuSCN, $CuCO_3$, $Cu(OH)_2$, $CuC_2O_4$, CuS, $Er(OH)_3$, $Eu(OH)_3$, $Ga(OH)_3$, $Hf(OH)_3$, $Ho(OH)_3$, $In(OH)_3$, $In_2S_3$, $FeCO_3$, $Fe(OH)_2$, $FeAsO_4$, $Fe(OH)_3$, $PbCO_3$, $PbCrO_4$, PbFe $(CN)_6$, $PbHPO_4$, $Pb(OH)_2$, $Pb(IO_3)_2$, $PbMoO_4$, $PbC_2O_4$, PbS, $Pb(OH)_4$, $Lu(OH)_3$, $Mg(OH)_2$, $Mg_3(PO_4)_2$, $MnCO_3$, $Mn(OH)_2$, $Hg_2Br_2$, $Hg_2CO_3$, $Hg_2Cl_2$, $Hg_2(CN)_2$, HgS, $NiCO_3$, $Ni_2P_2O_7$, $Pd(OH)_2$, $Pd(OH)_4$, $Pt(OH)_2$, $PtBr_4$, $PuF_3$, PoS, $KB(C_6H_5)_4$, $RaSO_4$, $AgN_3$, AgBr, AgCl, AgCN, $Ag_2C_2O_4$, $SrF_2$, $Sb_2S_3$, $SrWO_4$, $ZnCO_3$, and $ZnC_2O_4$. The first water-soluble solid salt AB(s) and the second water-soluble solid salt CD(s) for generating the above-mentioned precipitate may be appropriately selected.

For example, when the first water-soluble solid salt AB (s)—the second water-soluble solid salt CD (s) is BaCl—$Ag_2SO_4$, a precipitate generated by $BaCl_2$—$Ag_2SO_4$ may be $BaSO_4$—2AgCl. The first water-soluble solid salt AB(s) and the second water-soluble solid salt CD(s) for generating the above-mentioned precipitate will be readily understood and implemented by those skilled in the art.

In the above-described supply of water, the water may be supplied to completely fill a first solid salt chamber 111 and a second precipitation chamber 112 of the reverse electrodialysis device. For example, the reverse electrodialysis device may be supplied with water by dipping in water and being removed therefrom or injecting water with a syringe.

The above-described reverse electrodialysis device may further include an anode AD and a cathode CD facing each other, an oxidation chamber 113 formed the anode AD and one surface of the first cell stack 110, and a reduction chamber 114 formed between the cathode CD and the other surface of the first cell stack 110. In FIG. 1, an unexplained reference numeral R denotes a load. An oxidation reaction may occur in the oxidation chamber 113 to provide electrons, and a reduction reaction may occur in the reduction chamber 114 to receive the electrons.

Thus, the electrons may migrate from the anode AD to the cathode CD through the load R.

According to the above-described embodiment, since an activity ratio of a saturated high-salinity water portion and a low-salinity water portion, maintained by an ionic product constant of insoluble salt, is maintained for a certain period of time, power may be stably supplied without an additional pump.

Figure 2:
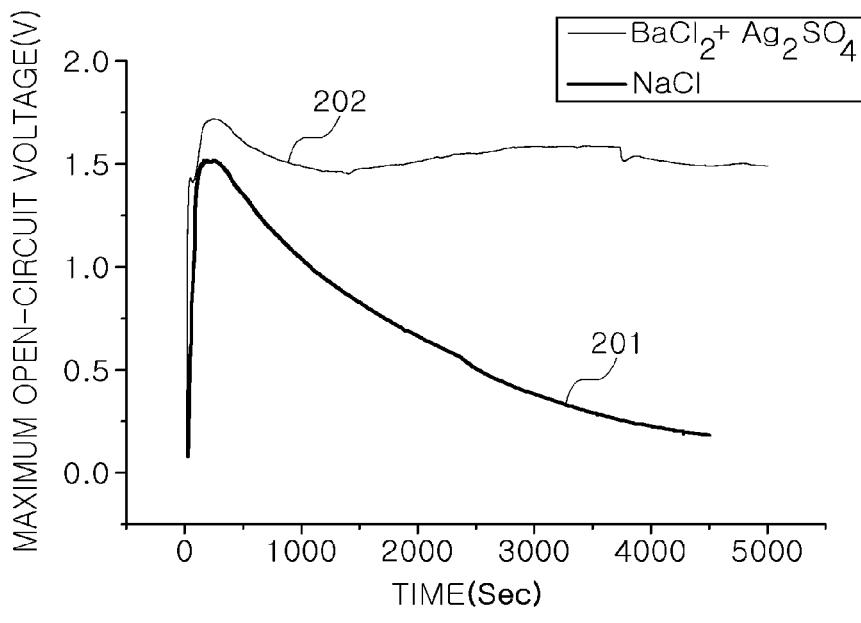
FIG. 2 illustrates a comparison between an open-circuit voltage of a reverse electrodialysis device according to an embodiment of the present disclosure and an open-circuit voltage of a conventional reverse electrodialysis device.

Specifically, FIG. 2 illustrates a comparison between an open-circuit voltage of a reverse electrodialysis device according to an embodiment of the present disclosure and an open-circuit voltage of a conventional reverse electrodialysis device.

In FIG. 2, a reference numeral 201 denotes an open-circuit voltage when single water-soluble salt in a solid state is introduced into a first chamber, and a reference numeral

202 denotes an open-circuit voltage when BaCl$_2$—Ag$_2$SO$_4$is used as first water-soluble salt-second water-soluble salt.

As illustrated in FIG. 2, in the case of the conventional reverse electrodialysis device, an open-circuit voltage is gradually decreased depending on time (see 201), whereas in the case of the reverse electrodialysis device according to this embodiment, an open-circuit voltage remains constant over time (see 202).

Figure 3:
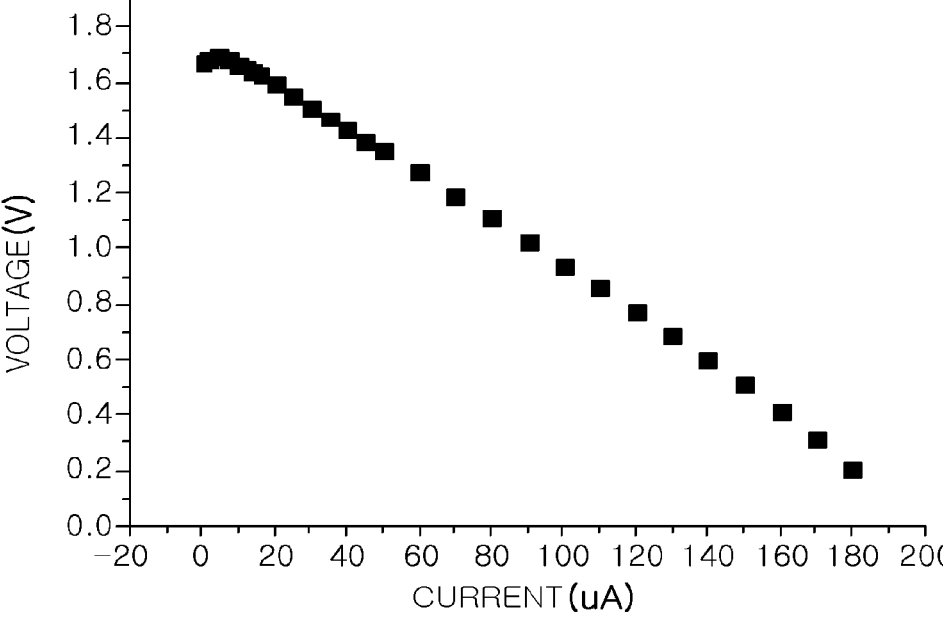
FIG. 3 illustrates a voltage when increasing current flowing from a reverse electrodialysis device according to an embodiment of the present disclosure.
Figure 4:
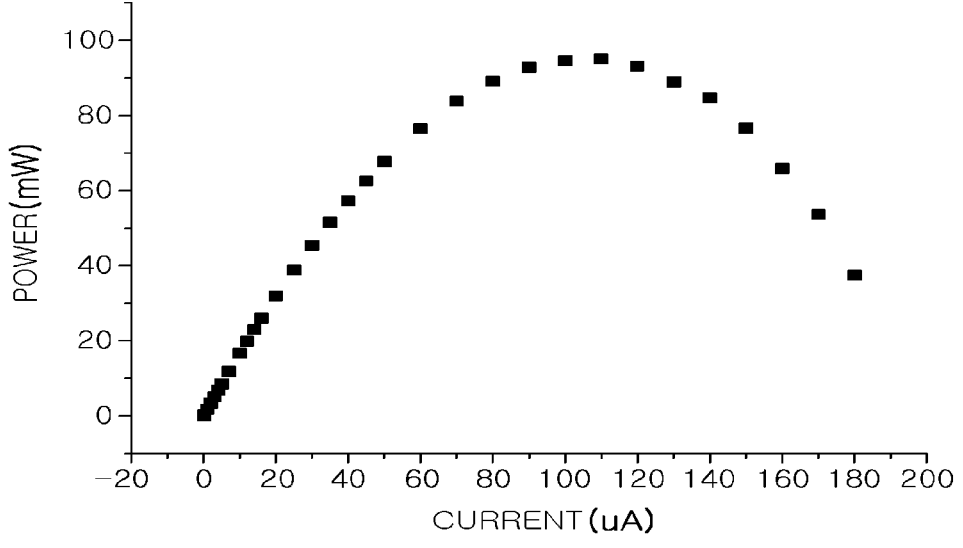
FIG. 4 is a power curve showing the voltage and the current of FIG. 3 in another manner.

FIG. 3 illustrates a voltage when increasing current flowing from a reverse electrodialysis device according to an embodiment, and FIG. 4 is a power curve showing the voltage and the current of FIG. 3 in another manner.

From FIG. 3, it can be seen that a reverse electrodialysis device according to an embodiment operates normally.

Figure 5:
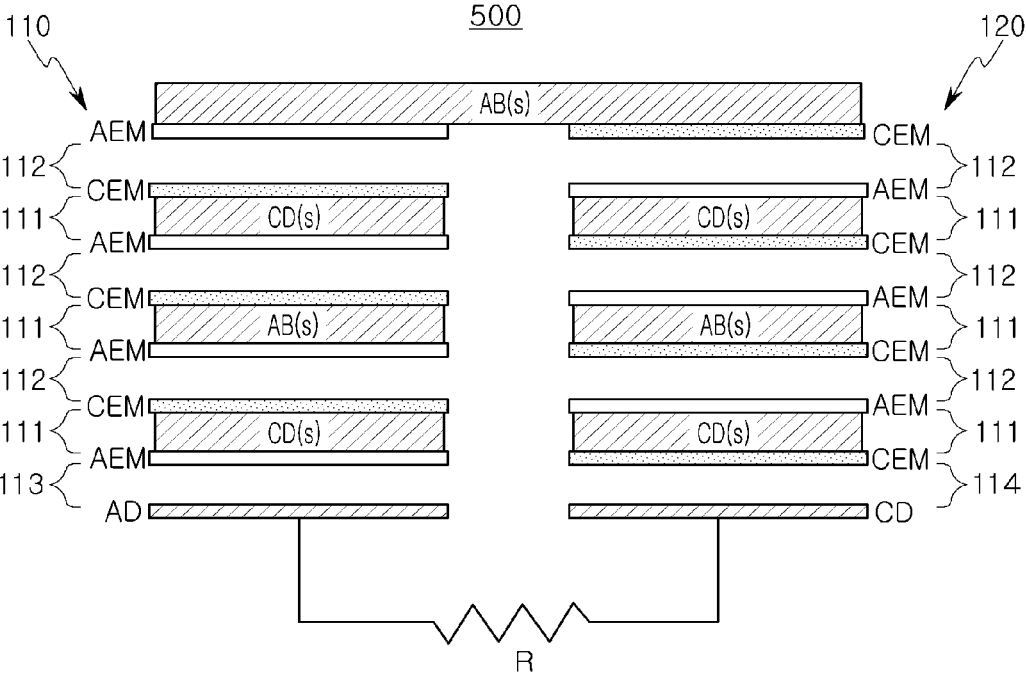
FIG. 5 illustrates a reverse electrodialysis device using a precipitation reaction according to another embodiment of the present disclosure.

FIG. 5 illustrates a reverse electrodialysis device 500 using a precipitation reaction according to another embodiment.

Unlike the reverse electrodialysis device illustrated in FIG. 1, the reverse electrodialysis device 500 includes a cell stack 120 configured in parallel such that two cell stacks 110 and 120 share either one of a sold salt chamber and a precipitation chamber.

Specifically, as illustrated in FIG. 5, the first cell stack 110 is provided with a solid salt chamber 111 and a precipitation chamber 112, alternately formed through a cation-exchange membrane CEM and an anion-exchange membrane AEM mounted alternately, and the solid salt chamber 111 is alternately filled with first water-soluble solid salt AB(s)-second water-soluble solid salt CD(s).

Similarly, the second cell stack 120 is provided with a solid salt chamber 111 and a precipitation chamber 112, alternately formed through a cation-exchange membrane CEM and an anion-exchange membrane AEM mounted alternately, and the solid salt chambers 111 is alternately filled with first water-soluble solid salt AB (s)-second water-soluble solid salt CD(s).

The first cell stack 110 and the second cell stack 120 are disposed on the same plane at regular intervals, and are configured to share either one of the solid salt chamber and the precipitation chamber on the other surfaces of the first cell stack 110 and the second cell stack 120. For better understanding of the present disclosure, in FIG. 5, a solid salt chamber is illustrated as being shared and a state, in which the solid salt chamber is filled with first water-soluble solid salt AB(s), is illustrated.

Likewise, the reverse electrodialysis device 500 may further include an anode AD and a cathode CD. An oxidation chamber 113 may be formed between one surface of the anode AD and the first cell stack 110, and a reduction chamber 114 may be formed between the cathode CD and the other surface of the second cell stack 120.

A precipitate, generated by the first water-soluble solid salt AB (s) and the second water-soluble solid salt CD(s), is the same as described in FIG. 1, and water may be supplied to completely fill the first solid salt chamber 111 and the second precipitation chamber 112 of the reverse electrodialysis device 500. For example, the reverse electrodialysis device 500 may be supplied with water by dipping in water and being removed therefrom or injecting water with a syringe.

The above-described reverse electrodialysis device may be applied to a small-sized power supply for driving a biosensor, a disposable sensor-integrated power supply, or a removable power supply.

As described above, according to an embodiment, a solid salt chamber of a cell stack is alternately filled with first water-soluble solid salt and second water-soluble solid salt. When water is supplied, the first water-soluble solid salt and the second water-soluble solid salt react with each other in a neighboring precipitation chamber to be precipitated while generating a precipitate. Thus, low-salinity water may be maintained at a low concentration to maintain a maximum open-circuit voltage at a constant level, and miniaturization of the device may be achieved without an additional pump.

Figure 6:
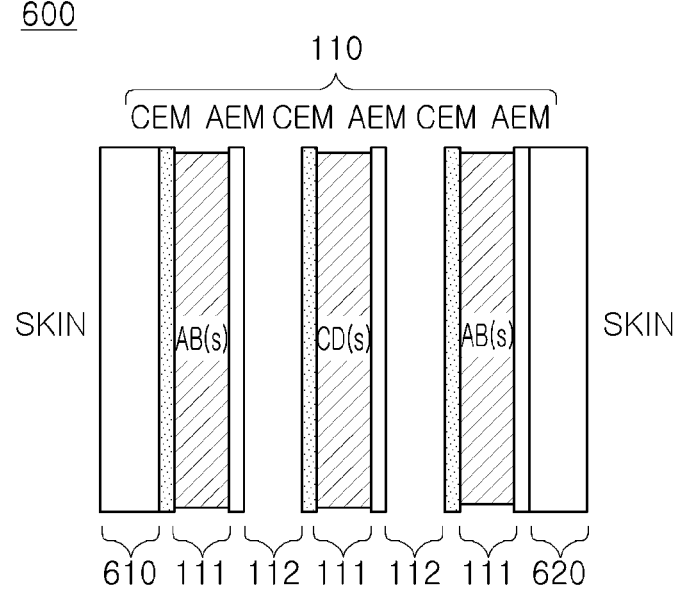
FIG. 6 illustrates a drug injection device according to an embodiment of the present disclosure.

FIG. 6 illustrates a drug injection device according to an embodiment of the present disclosure. The drug injection device, illustrated in FIG. 6, uses a precipitation reaction of the reverse electrodialysis device illustrated in FIG. 1.

Specifically, the drug injection device 600 may include a reverse electrodialysis device 110, generating current through a precipitation reaction between first water-soluble solid salt and second water-soluble solid salt, and material injection units 610 and 620 including a material having a charge or polarity and injecting the material having a charge or polarity into the skin by a voltage generated by the reverse electrodialysis device 110.

Specifically, in the first cell stack 110, a solid salt chamber 111 and a precipitation chamber 112 may be alternately formed through a cation-exchange membrane CEM and an anion-exchange membrane AEM mounted alternately to be spaced apart from each other at regular intervals. First water-soluble solid salt AB(s) and second water-soluble solid salt CD (s) fill the solid salt chamber 111. In detail, the first water-soluble solid salt AB(s) and the second water-soluble solid salt CD(s) may alternately fill the solid salt chamber 111. These chambers may be configured to prevent solid salts therein from escaping therefrom.

When water is supplied to the reverse electrodialysis device 110, cations A+ of the first water-soluble solid salt AB(s) may pass through the cation-exchange membrane CEM, and anions D$^-$ of the second water-soluble solid salt CD(s) may pass through the anion-exchange membrane AEM. The cations A+ and the anions D$^-$ may be precipitated in the neighboring precipitation chamber 112 while generating a precipitate AD(s) therein. Similarly, anions B$^-$ of the first water-soluble solid salt AB(s) and cations C+ of the second water-soluble solid salt CD(s) may be precipitated in the neighboring precipitation chamber 112 while generating a precipitate CB(s) therein.

Material injection units 610 and 620 may include a material having a charge or polarity, and may inject a material (a drug) having a charge or polarity into the skin by current generated by the reverse electrodialysis device 110. The material injection units 610 and 620 may be provided on at least one of one end and the other end of the cell stack 110.

For example, when water is supplied, the cations A+ of the first water-soluble solid salt AB(s) are released to the material injection unit 610 by the cation-exchange membrane CEM, and a material (a drug) having cations, included in the material injection unit 610, permeate the skin due to repulsive force.

Similarly, when water is supplied, the anions B$^-$ of the first water-soluble solid salt AB(s) are released to the material injection portion 620 by the anion-exchange membrane AEM, and a material (a drug) having anions, included in the material injection unit 620, permeate the skin due to repulsive force.

The material injection units 610 and 620 may be, for example, drug-containing hydrogel to be injected, and one surface thereof may be provided with an adhesive for smooth contact with the skin.

Figure 7:
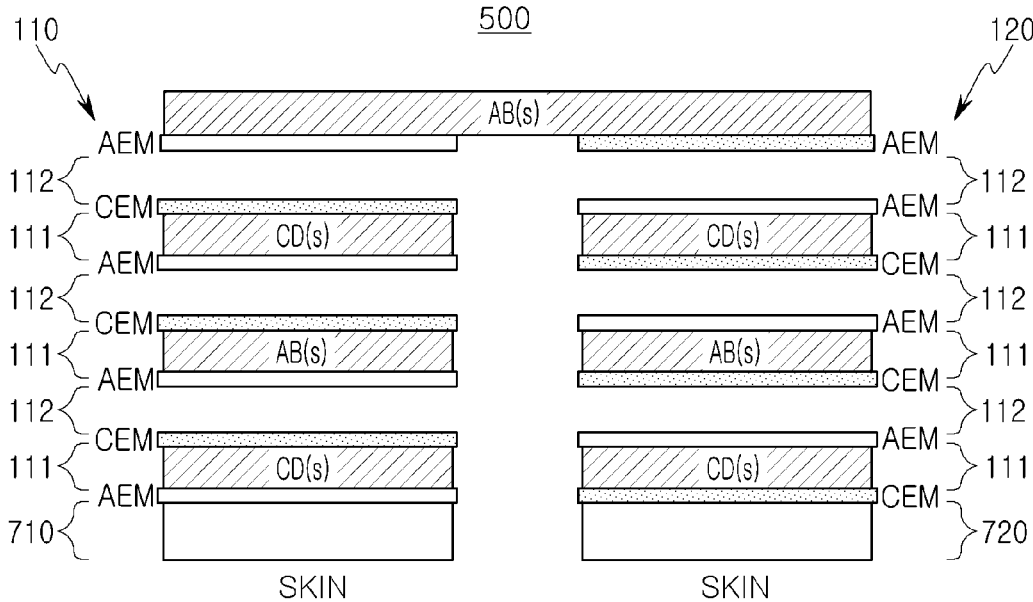
FIG. 7 illustrates a drug injection device according to another embodiment of the present disclosure.

FIG. 7 illustrates a drug injection device according to another embodiment of the present disclosure. The drug injection device illustrated in FIG. 7 uses a precipitation reaction of the reverse electrodialysis device illustrated in FIG. 5.

Specifically, as illustrated in FIG. 7, in a first cell stack 110, a solid salt chamber 111 and a precipitation chamber 112 may be alternately formed through a cation-exchange membrane CEM and an anion-exchange membrane AEM mounted alternately. First water-soluble solid salt AB(s) and second water-soluble solid salt CD(s) alternately fill the solid salt chamber 111.

Similarly, in a second cell stack 120, a solid salt chamber 111 and a precipitation chamber 112 may be alternately formed through a cation-exchange membrane CEM and an anion-exchange membrane AEM mounted alternately. First water-soluble solid salt AB(s) and second water-soluble solid salt CD(s) alternately fill the solid salt chamber 111.

When water is supplied to the above-described reverse electrodialysis devices 110 and 120, cations A+ of the first water-soluble solid salt AB(s) may pass through the cation-exchange membrane CEM and anions $D^-$ of the second water-soluble solid salt CD(s) may pass through the anion-exchange membrane AEM. The cations A+ and the anions $D^-$ may be precipitated in a neighboring precipitation chamber 112 while generating a precipitate AD(s) therein. Similarly, anions $B^-$ of the first water-soluble solid salt AB(s) and cations C+ of the second water-soluble solid salt CD(s) may be precipitated in the neighboring precipitation chamber 112 while generating a precipitate CB(s) therein.

Material injection units 710 and 720 may include a material having a charge or polarity, and may inject a material (a drug) having a charge or polarity into the skin due to current generated by the reverse electrodialysis devices 110 and 120. The material injection units 710 and 720 may be provided on at least one of one surface of the first cell stack 110 and one surface of the second cell stack 120.

For example, when water is supplied, the cations C+ of the second water-soluble solid salt CD(s) are released to the material injection part 720 by the cation-exchange membrane CEM, and a material (a drug) having cations, included in the material injection unit 720, permeates the skin due to repulsive force.

Similarly, when water is supplied, the anions $D^-$ of the second water-soluble solid salt CD(s) are released to the material injection unit 710 by the anion-exchange membrane (AEM), and a material (a drug) having anions, included in the material injection unit 710, permeate the skin due to repulsive force.

The above-described material injection units 710 and 720 may be, for example, a drug-containing hydrogel to be injected, and one surface thereof may be provided with an adhesive for smooth contact with the skin.

As described above, according to an embodiment, by applying the above-described principle of the reverse electrodialysis device using the precipitation reaction to the drug injection device, a drug may be delivered to the skin for a long period of time to improve performance of the device.

The scope of the present disclosure is not limited to the above-described embodiments and the accompanying drawings. It will be apparent to those skilled in the art that various replacements, modifications, and variations could be made without departing from the scope of the present disclosure as defined by the appended claims.

The invention claimed is:

1. A drug injection device comprising:
   a reverse electrodialysis device generating current through a precipitation reaction between first water-soluble solid salt and second water-soluble solid salt; and
   a material injection unit including a material having a charge or polarity and configured to inject the material having a charge or polarity into a skin by current generated by the reverse electrodialysis device,
   wherein the reverse electrodialysis device comprises:
   a first cell stack in which a plurality of solid salt chambers and a plurality of precipitation chambers are alternately formed and a plurality of cation-exchange membranes and a plurality of anion-exchange membranes are alternately formed, each solid salt chamber and each precipitation chamber formed through a cation-exchange membrane and an anion-exchange membrane;
   first water-soluble solid salt and second water-soluble solid salt alternately filling the solid salt chambers, and
   wherein, when the water is supplied, cations of the first water-soluble solid salt and anions of the second water-soluble solid salt are precipitated together in a precipitation chamber and anions of the first water-soluble solid salt and cations of the second water-soluble solid salt are precipitated together in a neighboring precipitation chamber.

2. The drug injection device of claim 1, wherein the precipitate includes at least two of $Ac(OH)_2$, $Al(OH)_3$, $As_2S_3$, $AgN_3$, $AgBr$, $AgCl$, $AgCN$, $Ag_2C_2O_4$, $Ba_3(AsO_4)_2$, $BaCO_3$, $BaCrO_4$, $Ba_2Fe(CN)_6$, $BaSO_4$, $BiAsO_4$, $Bi(OH)_3BiI_3$, $BiPO_4$, $Bi_2S_3$, $Cd_3(AsO_4)_2$, $CdCO_3$, $Cd_2Fe(CN)_6$, $Cd(OH)_2$, $Cd_3(PO_4)_2$, $CdS$, $Ca_3(AsO_4)_2$, $CaCO_3$, $CaC_2O_4$, $Ce(OH)_3$, $CePO_4$, $Ce(OH)_4$, $CoC_2O_4$, $CuCN$, $CuOH$, $CuI$, $Cu_2S$, $CuSCN$, $CuCO_3$, $Cu(OH)_2$, $CuC_2O_4$, $CuS$, $Er(OH)_3$, $Eu(OH)_3$, $Ga(OH)_3$, $Hf(OH)_3$, $Ho(OH)_3$, $In(OH)_3$, $In_2S_3$, $FeCO_3$, $Fe(OH)_2$, $FeAsO_4$, $Fe(OH)_3$, $PbCO_3$, $PbCrO_4$, $PbFe(CN)_6$, $PbHPO_4$, $Pb(OH)_2$, $Pb(IO_3)_2$, $PbMoO_4$, $PbC_2O_4$, $PbS$, $Pb(OH)_4$, $Lu(OH)_3$, $Mg(OH)_2$, $Mg_3(PO_4)_2$, $MnCO_3$, $Mn(OH)_2$, $Hg_2Br_2$, $Hg_2CO_3$, $Hg_2Cl_2$, $Hg_2(CN)_2$, $HgS$, $NiCO_3$, $Ni_2P_2O_7$, $Pd(OH)_2$, $Pd(OH)_4$, $Pt(OH)_2$, $PtBr_4$, $PuF_3$, $PoS$, $KB(C_6H_5)_4$, $RaSO4$, $AgN_3$, $AgBr$, $AgCl$, $AgCN$, $Ag_2C_2O_4$, $SrF_2$, $Sb_2S_3$, $SrWO_4$, $ZnCO_3$, and $ZnC_2O_4$.

3. The drug injection device of claim 1, wherein the material injection unit is disposed on at least one of one surface and the other surface of the first stack.

4. The drug injection device of claim 1, wherein the reverse electrodialysis device further comprises:
   a second cell stack in which a plurality of solid salt chambers and a plurality of precipitation chambers are alternately formed and a plurality of cation-exchange membranes and a plurality of anion-exchange membranes, each solid salt chamber and each precipitation chamber formed through a cation-exchange membrane and an anion-exchange membrane; and
   first water-soluble solid salt and second water-soluble solid salt alternately filling the solid salt chambers of the second cell stack, and
   wherein one surface of the first cell stack and one surface of the second cell stack are disposed on the same plane to be spaced apart from each other at regular intervals, and
   the other surface of the first cell stack and the other surface of the second cell stack share either one of a solid salt chamber and a precipitation chamber.

5. The drug injection device of claim 4, wherein the material injection unit is disposed on at least one of one surface of the first cell stack and one surface of the second cell stack.

6. The drug injection device of claim 1, wherein the water is supplied to completely fill the solid salt chamber and the precipitation chambers of the reverse electrodialysis device.

* * * * *